United States Patent [19]

Smith et al.

[11] 4,123,537

[45] Oct. 31, 1978

[54] 2-HALO-4-AMINOMETHYL-6-ALKYL-3-PYRIDINOLS USEFUL AS DIURETICS IN TREATING HYPERTENSION AND EDEMA

[75] Inventors: Robert L. Smith, Lansdale; Gerald E. Stokker, Gwynedd Valley; Edward J. Gragoe, Jr., Lansdale, all of Pa.

[73] Assignee: Merck & Co., Inc., Rahway, N.J.

[21] Appl. No.: 800,973

[22] Filed: May 26, 1977

[51] Int. Cl.² .................. A61K 31/345; C07D 213/65
[52] U.S. Cl. ................................. 424/263; 260/294.9; 260/296 R; 260/307 R
[58] Field of Search ..................... 424/263; 260/296 R

[56] References Cited

U.S. PATENT DOCUMENTS 4,029,816   6/1977   Cragoe et al. ..................... 424/316

OTHER PUBLICATIONS

Klingsberg, Pyridine and Derivatives, vol. 3, frontispage, pp. 659 and 772-775, Interscience Publishers (1962).
Burger, Medicinal Chemistry, 2nd Ed., frontispage and pp. 79-81, Interscience Publishers, Inc. NY (1960).
Burlakova et al., Chem. Abstracts, vol. 61, cols. 6020-6021 (1964).
Zhizhina, Chem. Abstracts, vol. 66, abst. 92175z (1967).
Odintsova, Chem. Abstracts, vol. 68, abst. 1091w (1968).

*Primary Examiner*—John D. Randolph
*Attorney, Agent, or Firm*—Michael C. Sudol, Jr.

[57] ABSTRACT

Certain substituted 4-aminomethyl-3-pyridinols and their pharmaceutically acceptacle acid addition salts wherein the pyridinol nucleus may be further substituted with 1 to 2 nuclear substituents are useful as antihypertensive, diuretic and saluretic agents. These products may be prepared by halogenating an appropriately substituted pyridine salt.

11 Claims, No Drawings

2-HALO-4-AMINOMETHYL-6-ALKYL-3-PYRIDINOLS USEFUL AS DIURETICS IN TREATING HYPERTENSION AND EDEMA

BACKGROUND AND SUMMARY OF THE INVENTION

This invention relates to a new class of chemical compounds which can be described generally as substituted 4-aminomethyl-3-pyridinols and to their non-toxic pharmaceutically acceptable acid addition salts.

Pharmacological studies indicate that the instant products are effective antihypertensive, diuretic and saluretic agents which can be used in the treatment of conditions associated with electrolyte and fluid retention and hypertension. When administered in a therapeutic dosage in conventional vehicles, the instant products effectively reduce the amount of sodium and chloride ions in the body, lower dangerous excesses of fluid to acceptable levels and, in general, alleviate conditions usually associated with edema and hypertension. Accordingly, their antihypertensive activity does not depend solely on their diuretic and saluretic properties.

The substituted 4-aminomethyl-3-pyridinols of this invention are compounds having the following structural formula:

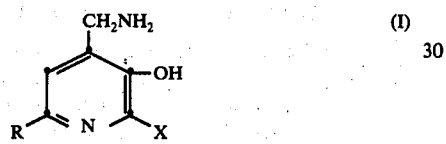

wherein
X is chloro, bromo, iodo or hydrogen;
R is straight or branched chain lower alkyl wherein the alkyl group has up to 5 carbon atoms;
and the non-toxic pharmaceutically acceptable acid addition salts thereof.

A more preferred embodiment of this invention are those compounds of Formula I wherein
X is chloro, bromo or iodo;
R is straight or branched chain lower alkyl wherein the alkyl group has 2 to 4 carbon atoms;
and the non-toxic pharmaceutically acceptable acid addition salts thereof.

The non-toxic pharmaceutically acceptable acid addition salts mentioned above are preferably the salts derived from non-toxic pharmaceutically acceptable acids such as hydrochloric acid, hydrobromic acid, hydriodic acid, sulfuric acid, methanesulfonic acid, isethionic acid and the like.

Preferred specific compounds of this invention can be
2-iodo-4-aminomethyl-6-(1,1-dimethylethyl)-3-pyridinol;
2-iodo-4-aminomethyl-6-(1-methylethyl)-3-pyridinol;
2-bromo-4-aminomethyl-6-(1,1-dimethylethyl)-3-pyridinol;
2-chloro-4-aminomethyl-6-(1,1-dimethylethyl)-3-pyridinol;
2-iodo-4-aminomethyl-6-(1,1-dimethylethyl)-3-pyridinol dihydrochloride.

The substituted 4-aminomethyl-3-pyridinols of this invention of Formula I can be prepared by the following synthetic method.

A N-acyl ester of glycine of the formula:

wherein R is as previously defined and $R_1$ is straight chain lower alkyl is dehydrated to give a substituted oxazole of the formula:

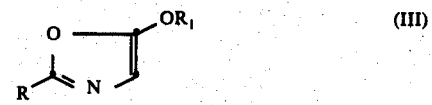

wherein R and $R_1$ are as previously defined which is then condensed with acrylonitrile to provide a substituted pyridine of the formula:

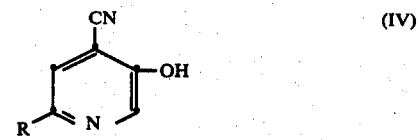

wherein R is as previously defined which is hydrogenated in the presence of a suitable acid to give salts of the formula:

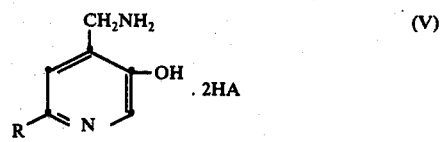

wherein R is as previously defined and A is a pharmaceutically acceptable anion which, in turn, is halogenated and then neutralized with a suitable base to afford the compounds of this invention of Formula I. Treatment of the latter with a nontoxic pharmaceutically acceptable acid gives the corresponding acid addition salt of the formula

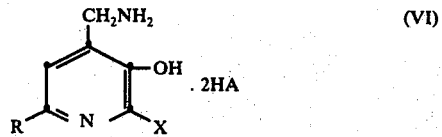

wherein R, X and A are as defined previously. A detailed description of this method follows.

(1) A N-acyl ester of glycine of formula II wherein R is as previously defined and $R_1$ is straight chain lower alkyl, preferably ethyl or methyl, is treated with a suitable dehydrating agent, preferably phosphorus pentoxide, in an inert solvent such as methylene chloride, chloroform, tetrahydrofuran and the like, preferably methylene chloride, at a temperature ranging between 20° C. and 100° C., preferably at the reflux temperature of the solvent, under an inert atmosphere for a period of 2 to 24 hours, preferably 6 to 8 hours. The resulting reaction mixture is treated with aqueous alkali, preferably 20% sodium hydroxide, and the product oxazole of formula III wherein R and $R_1$ are as previously defined is isolated by distillation.

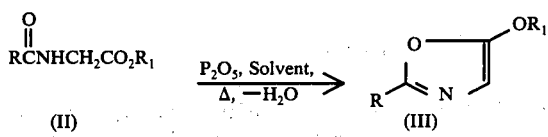

(2) An intimate mixture of an oxazole of Formula III and acrylonitrile is heated at a temperature ranging between 40° C. and 100° C., preferably 70°–75° C., for a period of 6 to 48 hours, preferably 12 to 24 hours, to give a substituted pyridine of Formula IV wherein R is as previously defined. The product IV is isolated by either chromatographing the reaction mixture on silica gel or distillation. The latter purification procedure involves distillation of unreacted III from the reaction mixture leaving the product IV as the pot residue which is readily purified by crystallization from a suitable solvent such as aqueous methanol.

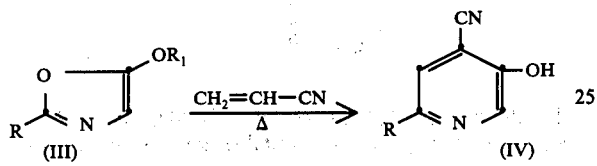

(3) Hydrogenation of a nitrile of Formula IV in a suitable solvent such as methanol, ethanol, ethyl acetate and the like, preferably ethanol, in the presence of a suitable acid, preferably hydrochloric acid, and a catalyst such as 10% palladium on charcoal in a Parr apparatus at room temperature and an initial pressure of 40–45 p.s.i. until the theoretical quantity of hydrogen is consumed affords the salt of Formula V wherein R and A are as previously defined after removal of the catalyst by filtration and the solvents by evaporation.

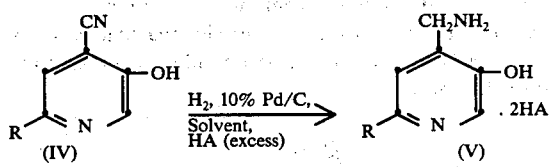

(4) A substituted pyridine salt of formula V is halogenated in a suitable protic, acidic medium such as dilute hydrochloric acid, aqueous acetic acid and the like with an appropriate halogenating agent, X—Y, in which X is as previously defined and Y is chloro, such as iodine monochloride, bromine monochloride, chlorine and the like at a temperature of 0° C. to 40° C., preferably at room temperature, for a period of 1 to 24 hours, preferably 8 to 18 hours. The product of Formula I wherein X and R are as previously defined is readily isolated by basification of the reaction solution with a suitable base, preferably ammonium hydroxide, whereupon I precipitates and is subsequently collected by filtration.

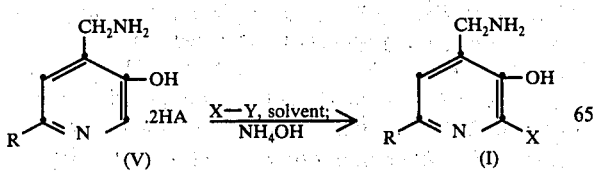

(5) The free base of Formula I is readily converted to the acid addition salt of formula VI wherein R, X and A are as previously defined by methods well known in the art, such as by reaction of the free base with the mineral acids mentioned previously in a suitable inert solvent at or about room temperature followed by removal of the solvent or dilution with a less polar, misible solvent to afford the salt.

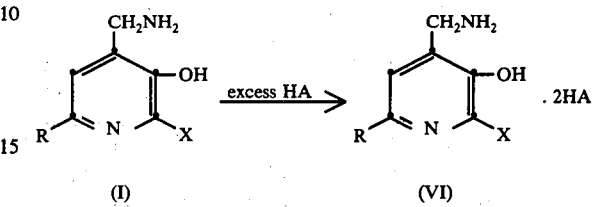

The examples which follow illustrate the substituted 4-aminomethyl-3-pyridinols of this invention and the method by which they are prepared.

EXAMPLE 1

Preparation of 2-Iodo-4-aminomethyl-6-(1,1-dimethylethyl)-3-pyridinol

Step A. Preparation of 2-(1,1-Dimethylethyl)-5-ethoxyoxazole

To a vigorously-stirred slurry of phosphorus pentoxide (163.8 g., 1.15 mole) in chloroform (600 ml.) maintained under a nitrogen atmosphere is added slowly a solution of ethyl N-pivaloylglycinate (107.8 g., 0.576 mole) in chloroform (350 ml.). Upon completing the addition, the reaction mixture is stirred and heated at reflux under a nitrogen atmosphere for 14 hours. The cooled reaction mixture is treated with 20% sodium hydroxide (800 ml.), vigorously stirred for ½ hour and allowed to separate into two phases. After discarding the aqueous phase, the organic phase is washed with water and saturated brine, dried over sodium sulfate and filtered. Distillation of the filtrate provides 2-(1,1-dimethylethyl)-5-ethoxyoxazole as a pale yellow liquid (64 g., 66%), b.p. 58°–64° C./0.7 mm.

Step B. Preparation of 4-Cyano-6-(1,1-dimethylethyl)-3-pyridinol

A neat mixture of 2-(1,1-dimethylethyl)-5-ethoxyoxazole (17 g., 0.1 mole) and acrylonitrile (6.1 g., 0.11 mole) is stirred and heated at 70°–75° C. for 16 hours. The resulting dark reaction mixture is cooled to 20° C. and chromatographed on silica gel (600 g.). Elution with 1% methanol in chloroform (4.35 l.) yields recovered 2-(1,1-dimethylethyl)-5-ethoxyoxazole (10.7 g., 63% recovery). Continued elution with the same eluant (300 ml.) affords impure product (3.2 g.). Further elution with the same eluant (2.5 l.) gives the desired product as a solid (6.5 g., 37%), m.p. 185°–195° C. Two recrystallizations of the latter from methanol-water (1:1; v:v) provides an analytical sample of 4-cyano-6-(1,1-dimethylethyl)-3-pyridinol as colorless crystals (4.5 g., 26%), m.p. 201°–202° C.

Step C. Preparation of 4-Aminomethyl-6-(1,1-dimethylethyl)-3-pyridinol . dihydrochloride A solution of 4-cyano-6-(1,1-dimethylethyl)-3-pyridinol (5.7 g., 0.032 mole) in methanol — 12N hydrochloric acid (30:1; v:v; 310 ml.) is hydrogenated in the presence of 10% palladium on charcoal (1 g.) in a Parr apparatus at 25° C. and 40–45 p.s.i. pressure until the theoretical quantity of hydrogen has been consumed. Then the hydrogenation mixture is filtered and the collected catalyst, washed with ethanol. Evaporation (in vacuo) of the combined filtrate and washings leaves the 4-aminomethyl-6-(1,1-dimethylethyl)-3-pyridinol dihydrochloride as a residual solid (7.9 g.; 98%), m.p. 304°–306° C. with dec. Recrystallization of the solid from ethanol-ether-water (100:100:4; v:v:v) affords an analytical sample of 4-aminomethyl-6-(1,1-dimethylethyl)-3-pyridinol dihydrochloride as colorless crystals, m.p. 304°–306° C. with dec.

Step D. Preparation of 2-Iodo-4-Aminomethyl-6-(1,1-dimethylethyl)-3-pyridinol

A solution of iodine monochloride (2.68 g., 0.02 mole) in 4N hydrochloric acid (15 ml.) is added to a solution of 4-aminomethyl-6-(1,1-dimethylethyl)-3-pyridinol . dihydrochloride (5.06 g., 0.02 mole) in water (30 ml.). The resulting solution is kept at 20°–25° C. for 18 hours, diluted with water to a volume of 100 ml. and basicified with concentrated ammonium hydroxide (12 ml.) whereupon a solid is deposited. The solid is collected, washed with water and air-dried to give 2-iodo-4-aminomethyl-6-(1,1-dimethylethyl)-3-pyridinol (4.8g., 78%), m.p. 162°–165° C. Recrystallization of the latter from 50% ethanol provides an analytical sample of 2-iodo-4-aminomethyl-6-(1,1-dimethylethyl)-3-pyridinol as pale beige crystals, m.p. 170°–171° C.

EXAMPLE 2

Preparation of 2-Iodo-4-aminomethyl-6-(1,1-dimethylethyl)-3-pyridinol dihydrochloride To a solution of 2-iodo-4-aminomethyl-6-(1,1-dimethylethyl)-3-pyridinol (4.8 g., 0.016 mole) in ethanol (50 ml.) is added 12N hydrochloric acid (3 ml.). The resulting solution is diluted slowly with ether (150 ml.) and cooled to 0°–5° C. whereupon a solid is deposited. The solid is collected, washed with ether and air-dried to give 2-iodo-4-aminomethyl-6-(1,1-dimethylethyl)-3-pyridinol dihydrochloride (5.4 g., 91%), m.p. 177°–179° C. with dec. Recrystallization from ether-ethanol-water (125:50:2; v:v:v) affords an analytical sample of the 2-iodo-4-aminomethyl-6-(1,1-dimethylethyl)-3-pyridinol dihydrochloride as colorless needles, m.p. 178°–179° C. with dec.

EXAMPLE 3

Preparation of 2-Iodo-4-aminomethyl-6-(1-methylethyl)-3-pyridinol

By following exactly the same procedures described in Example 1 but beginning with ethyl N-isobutrylglycinate instead of ethyl N-pivaloylglycinate, there are obtained successively:
Step A, 2-(1-methylethyl)-5-ethoxyoxazole;
Step B, 4-cyano-6-(1-methylethyl)-3-pyridinol;
Step C, 4-aminomethyl-6-(1-methylethyl)-3-pyridinol;
Step D, 2-iodo-4-aminomethyl-6-(1-methylethyl)-3-pyridinol.

EXAMPLE 4

Preparation of 2-Bromo-4-aminomethyl-6-(1,1-dimethylethyl)-3-pyridinol

This compound is prepared essentially by the same method as described in Example 1, Step D, except that the iodine monochloride is replaced by an equivalent quantity of bromine monochloride. Thereby is obtained 2-bromo-4-aminomethyl-6-(1,1-dimethylethyl)-3-pyridinol.

EXAMPLE 5

Preparation of 2-chloro-4-aminomethyl-6-(1,1-dimethylethyl)-3-pyridinol

This compound is prepared essentially by the same method as described in Example 1, Step D, except that the iodine monochloride is replaced by an equivalent quantity of chlorine. Thereby is obtained 2-chloro-4-aminomethyl-6-(1,1-dimethylethyl)-3-pyridinol.

EXAMPLE 6

Preparation of 2-iodo-4-aminomethyl-6-(1-methylethyl)-3-pyridinol dihydrochloride This compound is prepared exactly by the method described in Example 2 except that the 2-iodo-4-aminomethyl-6-(1,1-dimethylethyl)-3-pyridinol is replaced by an equivalent quantity of 2-iodo-4-aminomethyl-6-(1-methylethyl)-3-pyridinol. Thereby is obtained the 2-iodo-4-aminomethyl-6-(1-methylethyl)-3-pyridinol dihydrochloride salt.

EXAMPLE 7

Preparation of 2-Bromo-4-aminomethyl-6-(1,1-dimethylethyl)-3-pyridinol dihydrochloride This compound is prepared exactly by the method described in Example 2 except that the 2-iodo-4-aminomethyl-6-(1,1-dimethylethyl)-3-pyridinol is replaced by 2-bromo-4-aminomethyl-6-(1,1-dimethylethyl)-3-pyridinol. Thereby is obtained the 2-bromo-4-aminomethyl-6-(1,1-dimethylethyl)-3-pyridinol dihydrochloride salt.

EXAMPLE 8

Preparation of 2-Chloro-4-aminomethyl-6-(1,1-dimethylethyl)-3-pyridinol dihydrochloride This compound is prepared exactly by the method described in Example 2 except that the 2-iodo-4-aminomethyl-6-(1,1-dimethylethyl)-3-pyridinol is replaced by 2-chloro-4-aminomethyl-6-(1,1-dimethylethyl)-3-pyridinol. Thereby is obtained the 2-chloro-4-aminomethyl-6-(1,1-dimethylethyl)-3-pyridinol dihydrochloride salt.

The novel compounds of this invention are antihypertensive, diuretic and saluretic agents which can be administered in a wide variety of therapeutic dosages in conventional vehicles, as, for example, by oral administration in the form of a tablet or capsule, or by intravenous injection. Also the daily dosage of the products may be varied over a wide range varying from 5 to 2,000 mg.

The product is preferably administered in subdivided doses in the form of scored tablets containing 5, 10, 25, 50, 100, 150, 250 and 500 milligrams (most preferably 10 to 500 mg.) of the active ingredient for the symptomatic adjustment of the dosage to the patient to be treated. These dosages are well below the toxic or lethal dose of the products.

A suitable unit dosage form of the products of this invention can be formulated by mixing 50 milligrams of a substituted 2-halo-4-aminomethyl-3-pyridinol (I) or a suitable pharmaceutically acceptable acid addition salt thereof, with 149 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and, should it be necessary to mix more than 200 mg. of ingredients together, larger capsules may be employed. Compressed tablets, pills, or other desired unit dosages can be prepared to incorporate the compounds of this invention by conventional methods and, if desired, can be made up as elixirs or as injectable solutions by methods well known to pharmacists.

It is also within the scope of this invention to combine two or more of the compounds of this invention in a unit dosage form or to combine one or more of the compounds of this invention with other known diuretics and saluretics such as amiloride hydrochloride or with other desired therapeutic and/or nutritive agents in dosage unit form.

The following example is included to illustrate the preparation of a representative dosage form:

EXAMPLE 9

| Dry-filled capsules containing 50 mg. of active ingredient per capsule | |
| --- | --- |
|  | Per Capsule |
| 2-Iodo-4-aminomethyl-6-(1,1-dimethyl-ethyl)-3-pyridinol dihydrochloride | 50 mg. |
| Lactose | 149 mg. |
| Magnesium stearate | 1 mg. |
| Capsule (Size No. 1) | 200 mg. |

The 2-iodo-4-aminomethyl-6-(1,1-dimethylethyl)-3-pyridinol dihydrochloride is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds of this invention.

It will be apparent from the foregoing description that the substituted 2-halo-4-aminomethyl-3-pyridinols (I) and the pharmaceutically acceptable acid addition salts thereof of this invention constitute a valuable class of compounds which have not been prepared heretofore. One skilled in the art will also appreciate that the processes disclosed in the above examples are merely illustrative and are capable of a wide variation and modification without departing from the spirit of this invention.

What is claimed is:

1. A compound of the formula:

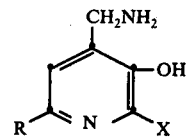

wherein
X is chloro, bromo or iodo;
R is straight or branched chain lower alkyl having up to 5 carbon atoms
and the non-toxic pharmaceutically acceptable acid addition salts thereof.

2. A compound of the formula:

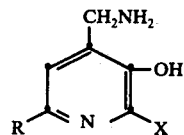

wherein
X is chloro, bromo or iodo;
R is a straight or branched chain lower alkyl having 2 to 4 carbon atoms; and
the non-toxic pharmaceutically acceptable acid addition salts thereof.

3. A compound of claim 2 being 2-iodo-4-aminomethyl-6-(1,1-dimethylethyl)-3-pyridinol.

4. A compound of claim 2 being 2-iodo-4-aminomethyl-6-(1,1-dimethylethyl)-3-pyridinol dihydrochloride.

5. A compound of claim 2 being 2-iodo-4-aminomethyl-6-(1-methylethyl)-3-pyridinol.

6. A compound of claim 2 being 2-bromo-4-aminomethyl-6-(1,1-dimethylethyl)-3-pyridinol.

7. A compound of claim 2 being 2-chloro-4-aminomethyl-6-(1,1-dimethylethyl)-3-pyridinol.

8. A pharmaceutical composition useful for the treatment of edema and hypertension which comprises a compound of the formula:

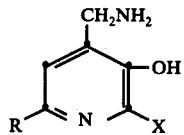

wherein
X is chloro, bromo or iodo;
R is straight or branched chain lower alkyl having up to 5 carbon atoms; or
the non-toxic pharmaceutically acceptable salts thereof and a pharmaceutically acceptable carrier.

9. A pharmaceutical composition useful for the treatment of edema and hypertension which comprises a compound of the formula:

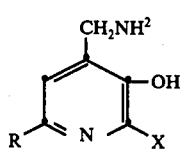

wherein
X is chloro, bromo or iodo;

R is a straight or branched chain lower alkyl having 2 to 4 carbon atoms;
or the non-toxic pharmaceutically acceptable salts thereof and a pharmaceutically acceptable carrier.

10. A method of treating edema and hypertension, which comprises administering to a patient in need of such treatment a pharmaceutically effective dose of a compound of the formula:

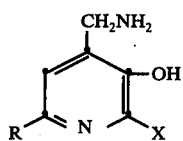

wherein
X is chloro, bromo, iodo or hydrogen;
R is straight or branched chain lower alkyl having up to 5 carbon atoms; or
a pharmaceutically acceptable acid addition salt thereof.

11. A method of treating edema and hypertension which comprises administering to a patient in need of such treatment a pharmaceutically effective dose of a compound of the formula

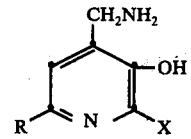

wherein
X is chloro, bromo or iodo;
R is a straight or branched chain lower alkyl having 2 to 4 carbon atoms; or
a pharmaceutically acceptable acid addition salt thereof.

* * * * *